(12) United States Patent
Belkerdid et al.

(10) Patent No.: US 9,063,058 B2
(45) Date of Patent: Jun. 23, 2015

(54) WIRELESS SURFACE ACOUSTIC WAVE CORROSION SENSOR AND INTERROGATION SYSTEM FOR CONCRETE STRUCTURES

(75) Inventors: Madjid A. Belkerdid, Casselberry, FL (US); Nikolai Y. Kozlovski, Orlando, FL (US); Donald Mark Haines, Melbourne, FL (US); Edwin Struble, Satellite Beach, FL (US)

(73) Assignee: Mnemonics, Inc., Melbourne, FL (US)

( * ) Notice: Subject to any disclaimer, the term of this patent is extended or adjusted under 35 U.S.C. 154(b) by 339 days.

(21) Appl. No.: 13/568,089

(22) Filed: Aug. 6, 2012

(65) Prior Publication Data
US 2013/0036821 A1 Feb. 14, 2013

Related U.S. Application Data

(60) Provisional application No. 61/515,020, filed on Aug. 4, 2011.

(51) Int. Cl.
*G01B 17/02* (2006.01)
*G01N 29/04* (2006.01)
*G01N 17/04* (2006.01)
*G01N 33/38* (2006.01)

(52) U.S. Cl.
CPC .............. *G01N 29/041* (2013.01); *G01N 17/04* (2013.01); *G01N 33/383* (2013.01)

(58) Field of Classification Search
CPC ....... G01H 5/00; G01B 17/02; G01N 29/041; G01N 17/04; G01N 33/383
USPC .................. 73/1.82, 40.5, 570.5; 324/637
See application file for complete search history.

(56) References Cited

U.S. PATENT DOCUMENTS

| 6,992,547 B2 | 1/2006 | Bergmann |
| 7,034,660 B2 * | 4/2006 | Watters et al. ............. 340/10.41 |
| 7,551,058 B1 | 6/2009 | Johnson |

(Continued)

FOREIGN PATENT DOCUMENTS

GB          2489048          9/2012

OTHER PUBLICATIONS

Malocha, D.C., Puccio D., Gallagher, D., [online], retrieved on Aug. 17, 2006, "Saw Sensors Using Orthogonal Frequency Coding," (2004) IEEE International Publication, 4 Pages, Retrieved from http://www.caat.engr.ufc.edu.

(Continued)

*Primary Examiner* — Laura Martin
*Assistant Examiner* — Suman K Nath
(74) *Attorney, Agent, or Firm* — John L. DeAngelis; Beusse Wolter Sanks & Maire, P.A.

(57) ABSTRACT

A SAW sensor disposed in on a material. The sensor comprises an antenna having a sacrificial link in at least one antenna element, wherein the sacrificial link is exposed to degrading elements within or on a surface of the material, a SAW transducer responsive to an interrogation signal for generating an incident acoustic wave, a reflector responsive to the incident SAW for creating a reflected SAW, the reflected SAW received by the transducer, the transducer for creating a response signal responsive to the reflected SAW, and the response signal transmitted from the antenna, characteristics of the response signal dependent on a condition of the sacrificial link.

11 Claims, 15 Drawing Sheets

(56) References Cited

U.S. PATENT DOCUMENTS

| | | | |
|---|---|---|---|
| 7,623,037 | B1 | 11/2009 | Malocha |
| 7,642,898 | B1 | 1/2010 | Malocha et al. |
| 7,986,218 | B2 | 7/2011 | Watters |
| 8,450,687 | B2* | 5/2013 | Lampin et al. ............ 250/339.07 |
| 2004/0123665 | A1* | 7/2004 | Blodgett et al. ................ 73/579 |
| 2006/0125697 | A1* | 6/2006 | Hung et al. ............ 343/700 MS |
| 2007/0046479 | A1* | 3/2007 | Hines ............................ 340/584 |
| 2009/0039864 | A1* | 2/2009 | Gordon ........................ 324/71.1 |
| 2009/0251375 | A1* | 10/2009 | Margomenos ................ 343/786 |
| 2010/0102670 | A1* | 4/2010 | Kashyap ................... 310/313 R |
| 2012/0007579 | A1* | 1/2012 | Apblett et al. ............... 324/71.1 |
| 2012/0174678 | A1* | 7/2012 | Gallagher et al. ............. 73/658 |

OTHER PUBLICATIONS

Malocha, D.C., Puccio, D., Gallagher D., "Orthogonal Frequency Coding for Saw Device Applications," Ultrasonic Symposium, (2004) IEEE vol. 2, Aug. 23-27, 2004, pp. 1082-1085, vol. 2 Digital Object Identifier 10.1109/ULTSYM.2004.1417965.

Zhijun Zhang, Madgy F. Iskander, Jean Christophe Langer and Jim Mathews "Dual Band WLAN Dipole Antenna Using an Internal Matching Circuit", IEEE Transactions on Antennas and Propagation, vol. 53, No. 5, May 2005.

Freescale Semiconductor Application Note, Document No. AN2731 Rev 1.3 Jan. 2006, Publication, 26 pages pdf., Retrieved from online site.

* cited by examiner

WIRELESS SURFACE ACOUSTIC WAVE CORROSION SENSOR AND INTERROGATION SYSTEM FOR CONCRETE STRUCTURES

CROSS REFERENCE TO RELATED APPLICATIONS

The present invention claims priority under 35 U.S.C. 119 (e) to the provisional application filed on Aug. 4, 2011, assigned application No. 61/515,020 and entitled Wireless Surface Acoustic Wave Corrosion Sensor and Interrogation System for Concrete Structures. This provisional patent application is incorporated in its entirety herein.

BACKGROUND OF THE INVENTION

The prior art is depicted in FIGS. 1 through 10.

FIG. 1 depicts a prior art passive wireless SAW (surface acoustic wave) sensor, an antenna and reflectors disposed on a material of interest, e.g., metal, concrete, plastic or any material that propagates RF signals. An RF interrogating signal is received by the sensor and responsive thereto a SAW transducer creates a SAW wave. The SAW wave signal propagates through the material and is reflected from the reflectors back to the antenna. From the antenna the reflected signal is propagated to the remote interrogating antenna for processing.

Characteristics of the reflected signal (e.g., time delay, propagation losses, phase delay) indicate certain characteristics of the material of interest, including a material temperature, forces, stresses, strains, etc. exerted on the material.

FIG. 2 depicts a wireless passive SAW sensor network and its components comprising: an RF wireless SAW interrogator, a controlling computer (depicted as a laptop computer in FIG. 2), an interrogating antenna for transmitting the interrogating signal to the SAW sensor and receiving the response from the sensor, and a plurality of remote SAW sensors (four illustrated) disposed in or on a material of interest.

FIG. 3 illustrates RF SAW sensor responses from a four-sensor network system of FIG. 2. The sensor echoes are in this case separated in time, but may overlap if certain signal coding schemes are used. This system can function with any number of sensors and is thus not limited to four sensors.

FIG. 4 illustrates an RF return echo of a single sensor in a system comprising a plurality of sensors, such as the sensor system of FIG. 2. Again, the number of sensors is limited only by desired performance, application, complexity, and cost.

FIGS. 5(a) through 5(d) illustrate several exemplary dipole PCB (printed circuit board) antennas for construction on a printed circuit board substrate. The SAW device is typically installed in a chip carrier package with two leads exiting the package for soldering to each of the two illustrated antenna terminals 20 and 21.

FIG. 5(a) depicts a common linear dipole antenna having a trace width W that affects the sensor bandwidth and a length $\lambda/2$ that affects the antenna gain and resonant frequency.

FIG. 5(b) depicts a dual slope slanted dipole antenna.
FIG. 5(c) depicts a single slope slanted dipole antenna.
FIG. 5(d) depicts a folded dipole antenna.

FIG. 6 depicts a SAW device 22 comprising a transducer 24 mounted on a substrate 25 and attached through two bond wires 28 and 29 to two pins 30 and 32 of a chip carrier 33 (header), a plurality of reflectors 35, and a lid 36 for hermetically sealing to a chip carrier package 38.

FIG. 7 depicts a dipole antenna 40 for use with a packaged SAW sensor for soldering on a top surface of the header. The dipole antenna 40 can be formed on FR4 PCB material 44.

FIG. 8 depicts a SAW sensor 48 soldered to the dipole antenna 40 absent a lid. FIG. 8 also illustrates sensor pins 50 soldered to antenna terminals 54.

FIG. 9 depicts the SAW sensor 48 of FIG. 8 with a lid 58 in place. Note that in both FIGS. 8 and 9 a small horizontal pad 60 at a bottom surface of the sensor 48 provides mechanical stability when the chip carrier 38 is soldered to a pad.

BRIEF DESCRIPTION OF THE FIGURES

The embodiments of the present invention can be more easily understood and the advantages and uses thereof more readily apparent when the following detailed description of the present invention is read in conjunction with the figures wherein.

DETAILED DESCRIPTION OF THE INVENTION

Figure 1:
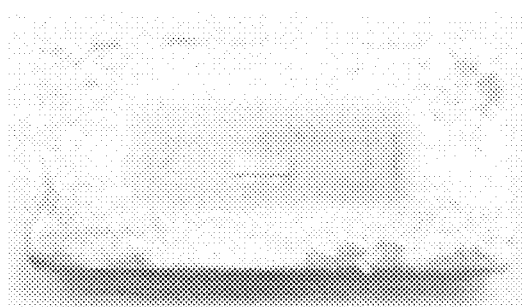
FIG. 1 is a photograph of a prior art SAW sensor.
Figure 2:
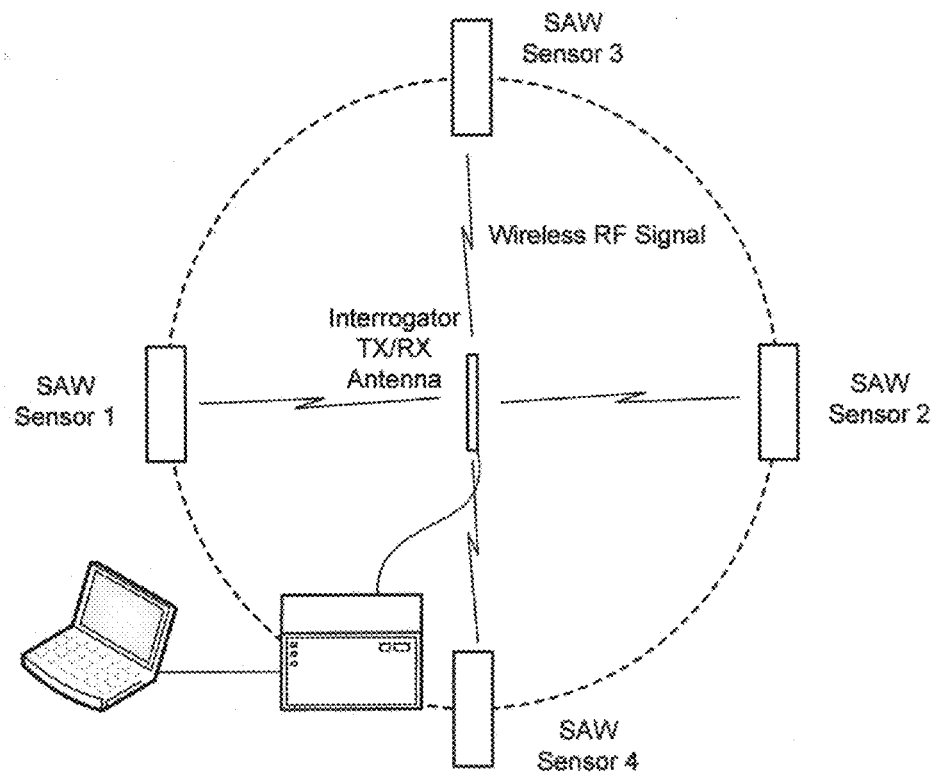
FIG. 2 illustrates a wireless sensing system of the prior art.
Figure 3:
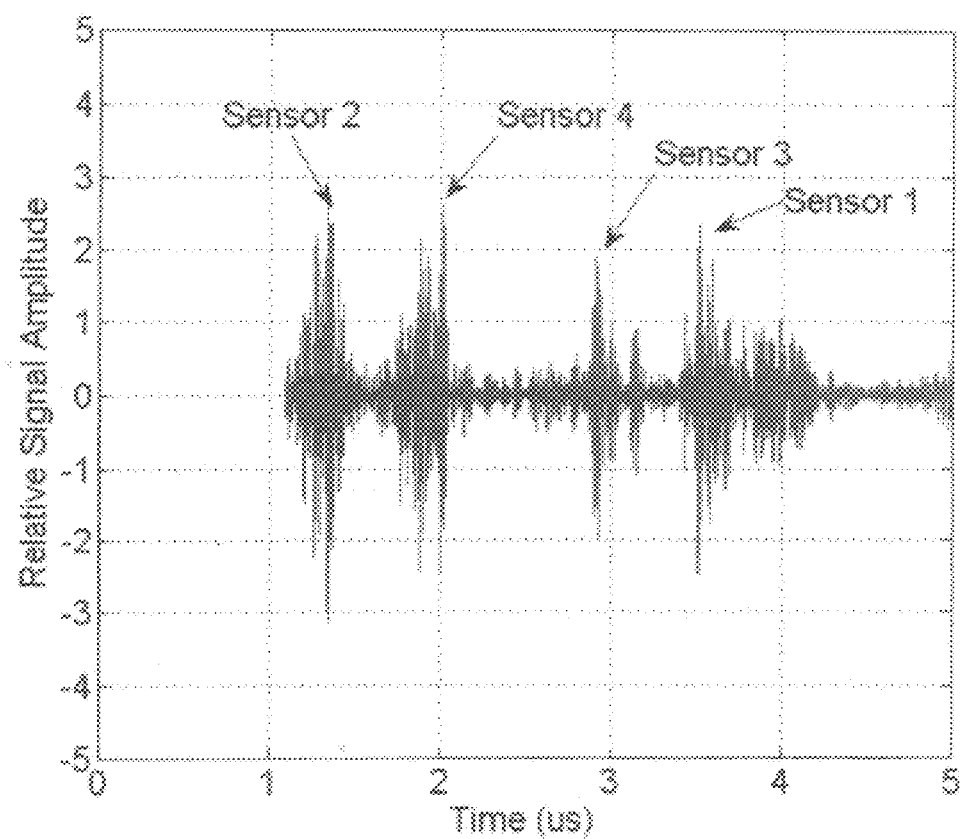
FIGS. 3 and 4 illustrate responses of sensors according to the prior art.
Figure 4:
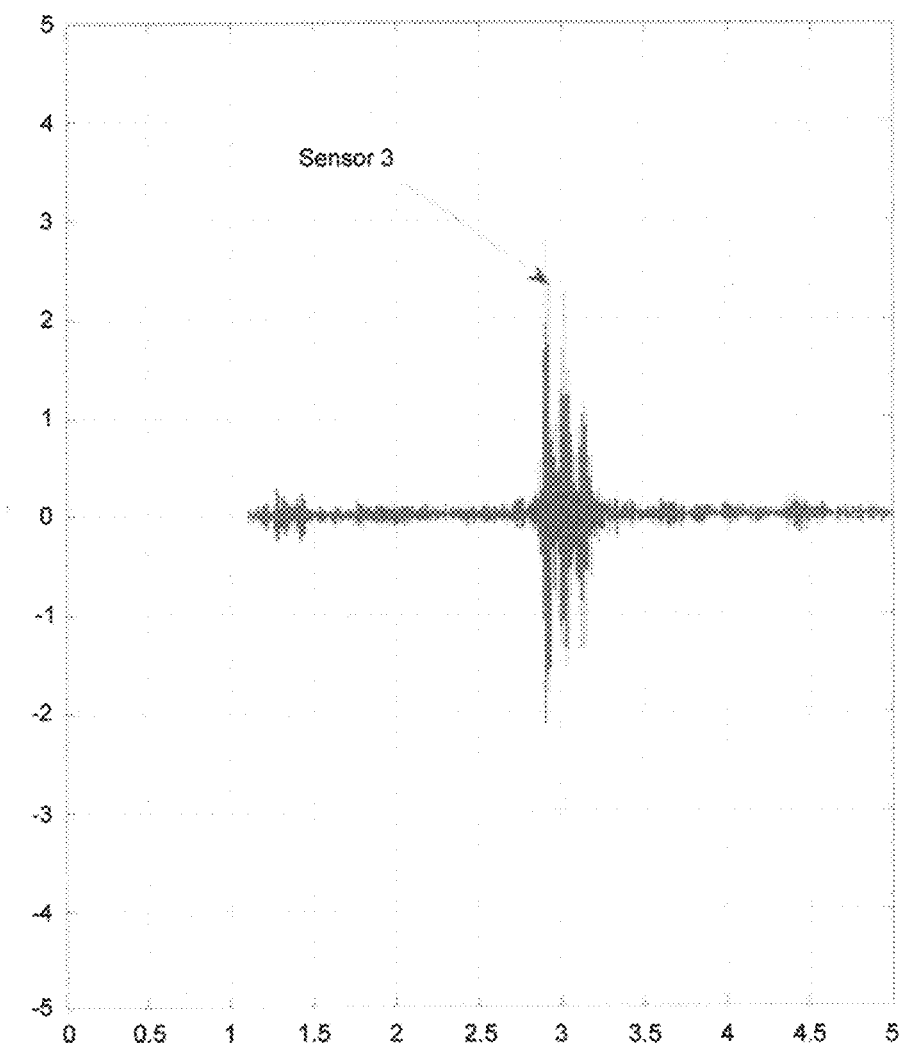
Figure 5A:
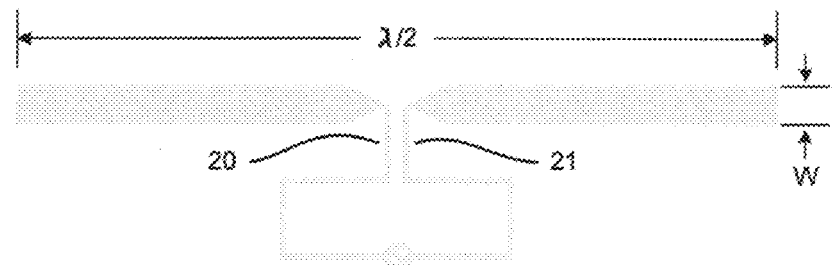
FIGS. 5(a) through 5(d) illustrate dipole antenna configurations according to the prior art.
Figure 5B:
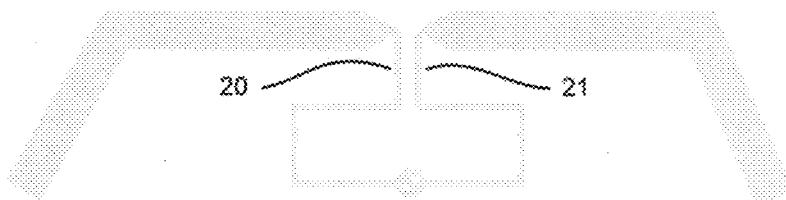
Figure 5C:
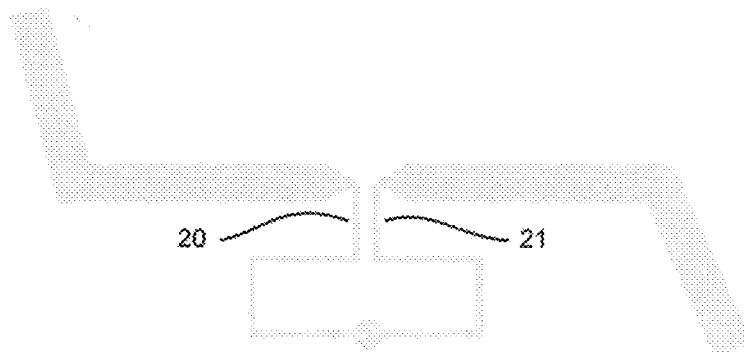
Figure 5D:
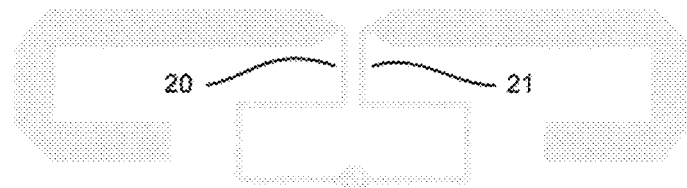
Figure 6:
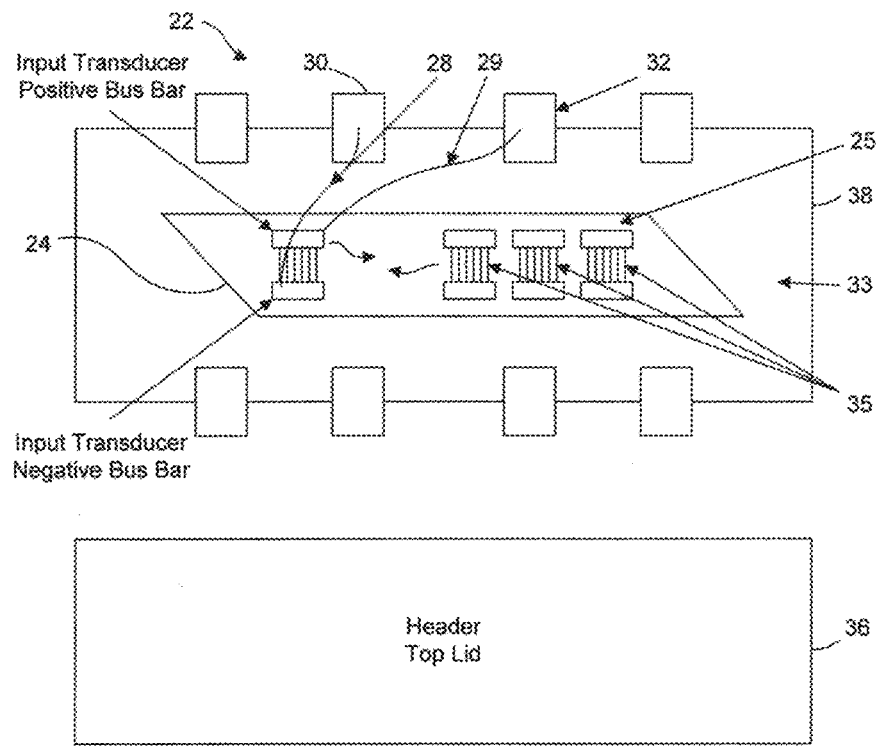
FIG. 6 illustrates SAW device attached to a chip header and a header lid according to the prior art.
Figure 7:
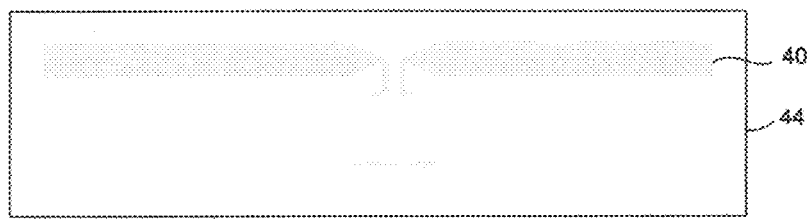
FIG. 7 illustrates a dipole antenna and feed for a SAW device according to the prior art.
Figure 8:
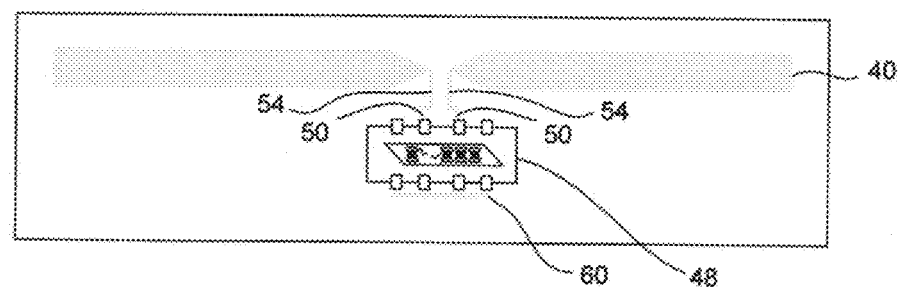
FIG. 8 illustrates a SAW device connected to a dipole antenna according to the prior art.
Figure 9:
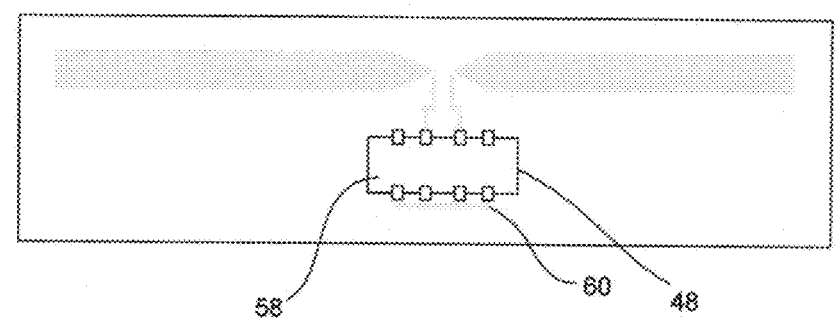
FIG. 9 illustrates the SAW device of FIG. 8 with the lid attached.

While preferred embodiments of the present invention are described and illustrated herein, it will be obvious that such embodiments are provided by way of example only. Numerous variations, changes and substitutions will occur to those of skill in the art without departing from the invention. Accordingly, it is intended that the invention be limited only by the spirit and scope of the appended claims.

Prior art corrosion sensors use probes made of material similar to the material of reinforcing rebars. These probes require routing electrical wires in and out of the concrete structures. This invasive technique may degrade or damage the structure to be monitored. Other sensors use electrochemical devices that require frequent recalibration. Surface acoustic wave (SAW) sensors are passive, wireless, and rugged, thus making them good candidates for corrosion monitoring of steel-reinforced concrete structures.

The present invention comprises a wireless sensor for corrosion monitoring of steel-reinforced concrete structures using embedded surface acoustic wave devices with a dipole antenna having at least one sacrificial corrosive link. The SAW device characteristics are not necessarily used as a sensing mechanism, but instead comprise a sacrificial corrosive link that, according to different embodiments, can make or break an RF interrogation signal path between an RF interrogator and a SAW device. For example, the corrosive link(s) can be disposed within a dipole antenna element or in the signal path between the antenna and the SAW device. The SAW device/sensor is embedded in or disposed on a surface a concrete structure that is monitored for corrosion degradation. These sacrificial corrosive links (e.g., steel bridges) are made of a material having similar properties (e.g., a same steel grade) as a concrete rebar and thus corrode at about the same rate as the rebars.

In one embodiment the sacrificial corrosive link serves as a circuit link such that when the link corrodes and opens, the circuit is disabled by this interruption in the signal path. Thus a response signal cannot be transmitted from the SAW sensor in response to an interrogation signal.

According to another embodiment the corrosive link degrades with time, opens and allows the sensor to communicate via an RF signal with the interrogator.

An exemplary frequency of about 915 MHz can be used in one embodiment of the present invention, but scaling laws apply for other frequencies such as 2.4 GHz or higher or lower frequencies.

The three principal components of the current invention comprise: an RF interrogator system, a SAW device, and a modified dipole antenna. The dipole antenna receives and transmits signals to/from the interrogation system only until the sacrificial link corrodes and opens the circuit link.

The RF interrogation system comprises a transmitter for generating an RF pulsed signal at a synchronous frequency or frequencies and at an appropriate bandwidth and power level for use with the SAW sensor. The interrogation system further includes a transmit/receive antenna and a receiver capable of detecting and processing the echo signals (return signals) emanating from the SAW device and its attendant antenna.

The second component is a SAW device comprising a reflector structure similar to the devices used in RFID systems. These SAW devices comprise an input inter-digitated transducer with positive electrodes connected to a positive bus bar and negative electrodes connected to a negative bus bar. Two dipole antenna terminals are connected to the positive and negative bus bars. When the RF interrogation signal is received by the dipole antenna a surface wave is launched on both sides of the input transducer. A bank of reflectors some distance away on one side or both sides of the input transducer reflect the surface wave back to the input transducers and out to the dipole antenna which in turn will transmits this echo or return signal back to the RF interrogator. The reflector bank can operate at a single frequency such as in a CDMA RFID tag system or at multiple frequencies such as used in OFC (orthogonal frequency coding) system.

The third component is the inventive dipole antenna that contains a corrosion sensing mechanism (i.e., sacrificial link) in one or both of the dipole antenna segments. A balanced (differential) generator supplies a signal to the antenna center terminals. When one or both of the sacrificial links corrode and open, antenna operation is severely degraded and no or a very small magnitude return signal is transmitted back to the interrogation system. A magnitude of the return signal may be responsive to a degree of degradation of the sacrificial link and thus indicative of the degree of corrosion of the material in which the sacrificial link is embedded or disposed upon.

A suitable dipole antenna can also be fabricated on a PCB by forming a copper pattern, similar to the two wire structure, by using known copper etching techniques and incorporating a sacrificial link into one or both of the dipole segments.

An etching process controls a dipole length and width as formed on one surface of an FR4 substrate (a common material from which printed circuit boards are formed) that supports the antenna conductive layer. In one embodiment the dipole antenna is formed on a 30 mil thick FR4 substrate using 0.5 oz copper (0.7 mil thick). This antenna is resonant, or non-reactive, at a frequency where the total pattern length is ½ wavelength. For operation in the 900 MHz ISM band, this length is approximately 17 cm (6.56 inches). The antenna bandwidth depends on the width of the pattern and the amount for a given return loss level.

The free space radiation pattern is the conventional doughnut-shaped pattern, with pronounced dips along a length direction of the dipole antenna. To improve the antenna radiation pattern and reduce the antenna's physical size, the terminal ends of the antenna can be bent up and/or down, at a 45 degree angle for example, or folded as shown in FIGS. 5(a) through 5(d).

A SAW device and a dipole antennas having no active elements are well-suited for extended term durability, such as when embedded in a material of interest.

The SAW device and its attendant dipole antenna built on an FR4 PCB substrate are designed to be chemically isolated from exposure to the material (e.g., concrete) in which the device is embedded by applying a conformal coating, insulation layer or passivation layer over the device (with the exception of the sacrificial link). These coatings have a minimal effect on the RF signal transmission and reception to/from the SAW device.

The insulating or protective coat is applied in such a manner to isolate the SAW device and its dipole antenna, except for the sacrificial links in the antenna. These links are exposed to the corroding elements that seep into the concrete or other material of interest and when the sacrificial links corrode the RF path is broken and the SAW device can no longer respond to the RF interrogation signal. Thus corrosion has been detected.

The invention is operation and function of the invention is further described in conjunctions with the following figures as described below.

Figure 10:
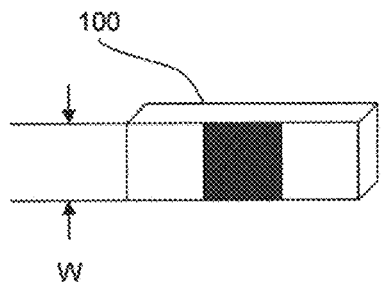
FIG. 10 illustrates a corrosive or sacrificial link for use with the present invention.

FIG. 10 illustrates a corrosive or sacrificial link 100. A link width W is dictated by a system bandwidth. A length and thickness affects the corrosion rate. Different widths, heights, and thicknesses are possible to accommodate different frequency bands and different applications.

Figure 11:
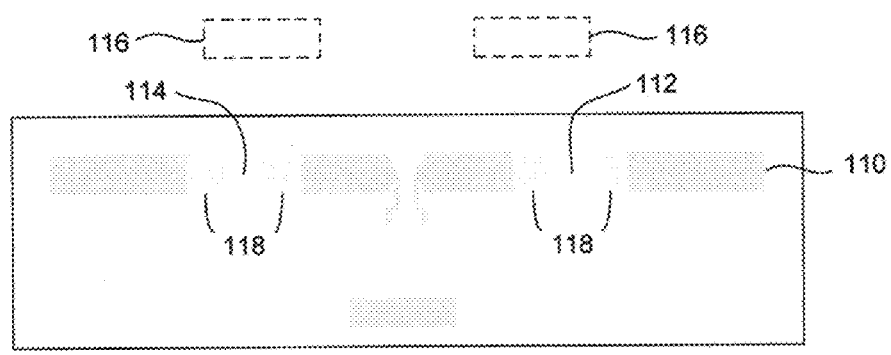
FIG. 11 illustrates a dipole antenna for use with the present invention.

FIG. 11 illustrates a dipole antenna 110 with two gaps 112 and 114 formed in the conductive pattern thereof. A sacrificial or corrosive link 116 is placed across each gap 112/114 and soldered to bridge each gap at solder pads 118.

Figure 12:
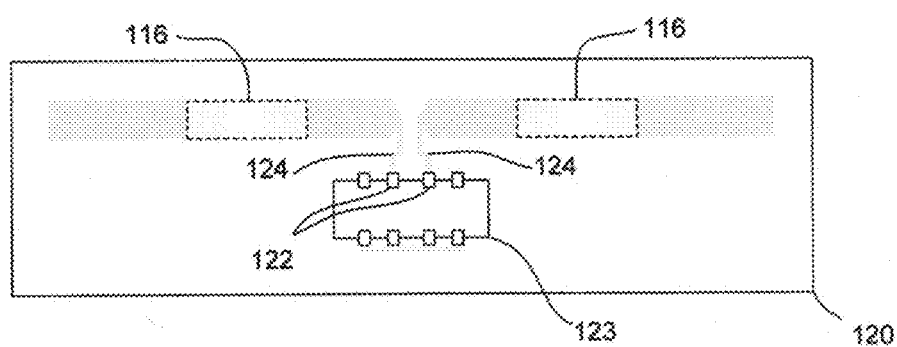
FIG. 12 illustrates a SAW sensor constructed according to the teachings of the present invention.

FIG. 12 depicts an assembled wireless SAW corrosion sensor 120 of the present invention. The sacrificial links 116 have been soldered in place and terminals 122 of the SAW sensor package 123 have been soldered to antenna terminals 124.

Figure 13:
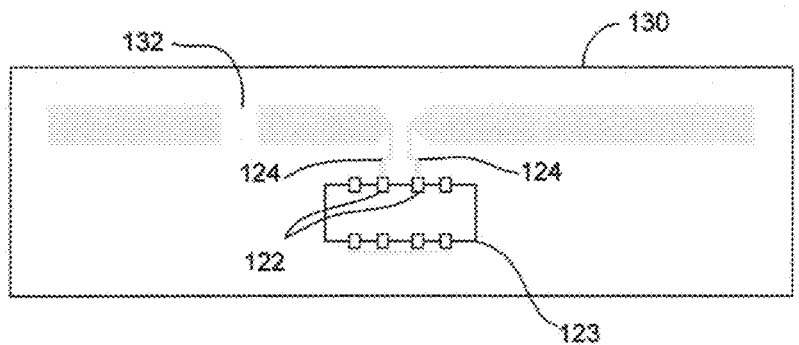
FIGS. 13 and 14 illustrate a SAW sensor having a single corrosive link.

FIG. 13 depicts an embodiment of an assembled wireless SAW corrosion sensor 130 comprising a single sacrificial link 132. The sacrificial link 132 has been soldered in place and the SAW sensor package terminals 122 have been soldered to the antenna terminals 124. This single sacrificial link embodiment allows the corrosion sensor to transmit an RF signal at about one-half power, instead of no RF return or response signal in an embodiment with a corrosive link in both antenna legs. In the latter case, when both sacrificial links have been corroded and present open circuits a return RF signal cannot be transmitted.

Figure 14:
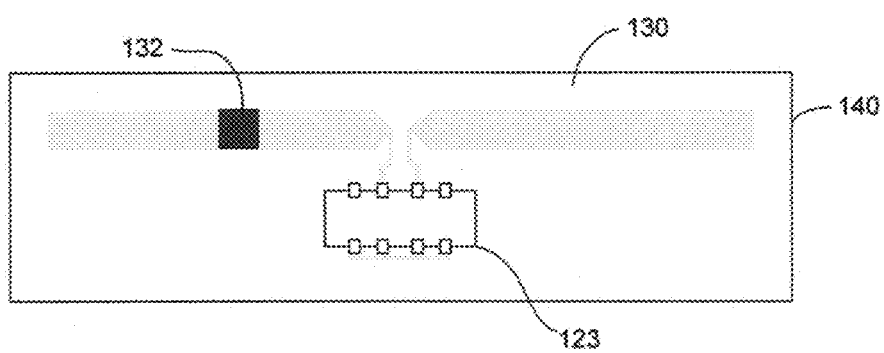

FIG. 14 depicts the wireless SAW corrosion sensor 130 of FIG. 13 with a protective coating 140. The entire device, including both surfaces of the substrate, the dipole antenna, and the sensor package are enclosed in a protective material such as conformal coating or epoxy-type material coating. Of course the sacrificial link 132 must be exposed to the same environmental conditions as the concrete and rebar structures (or any structures in which the sensor is mounted) that it monitors and therefore is not enclosed within any protective coating or layer. The sacrificial link is the only element of the corrosion sensor in contact with its surroundings. Therefore when the material of interest is concrete, the sacrificial link is the only element that is in contact with the chlorides that seep into the concrete and generate corrosion or produce a corrosive effect. Although a conformal coating has been described as the isolating material for the remainder of the sensor, the invention is not limited to a conformal coating.

Figure 15:
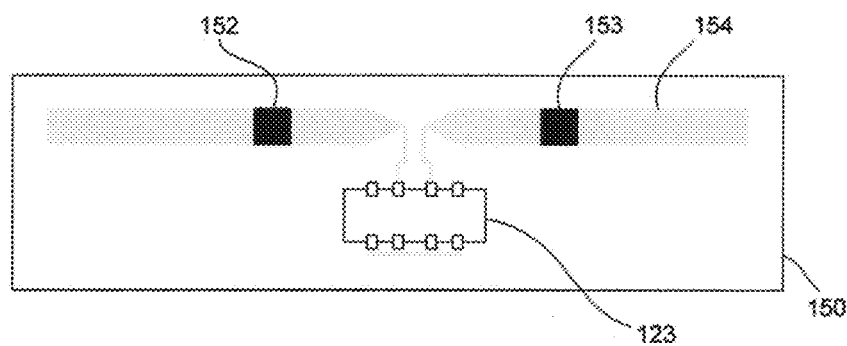
FIGS. 15 and 16 illustrate a SAW sensor having two sacrificial links.

FIG. 15 depicts another embodiment of a SAW corrosion sensor 150 having two sacrificial links 152 and 153 within a dipole antenna 154 before application of a conformal coating.

Figure 16:
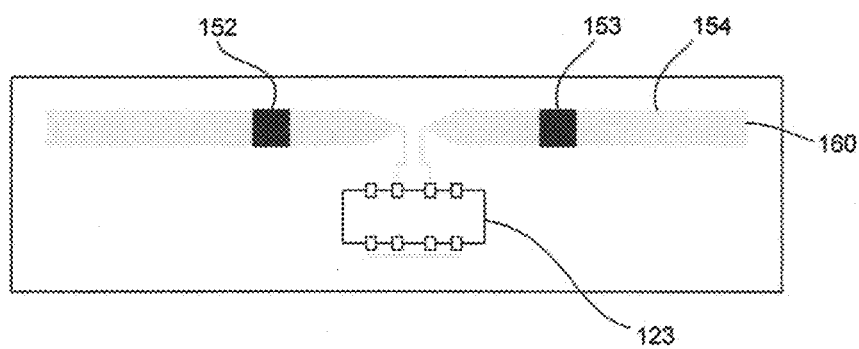

FIG. 16 depicts the embodiment of FIG. 15 after application of a protective coating 160, except over the unprotected sacrificial links 152 and 153.

Figure 17:
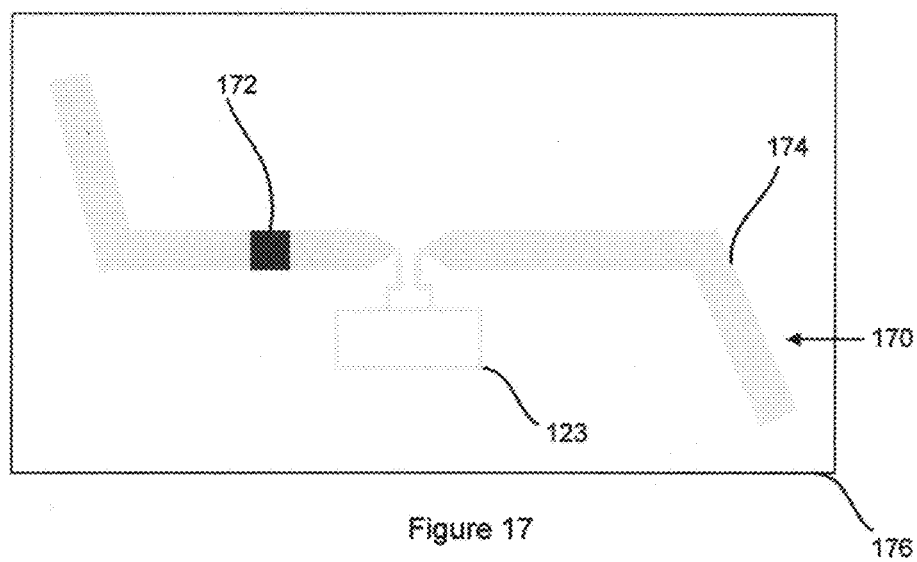
FIG. 17 illustrates a SAW sensor having a single sacrificial link in a single slanted dipole antenna.

FIG. 17 depicts an embodiment of a SAW corrosion sensor 170 with a single (exposed) sacrificial link 172 within a dual slope slanted dipole antenna 174 after application of a conformal coating 176.

Figure 18:
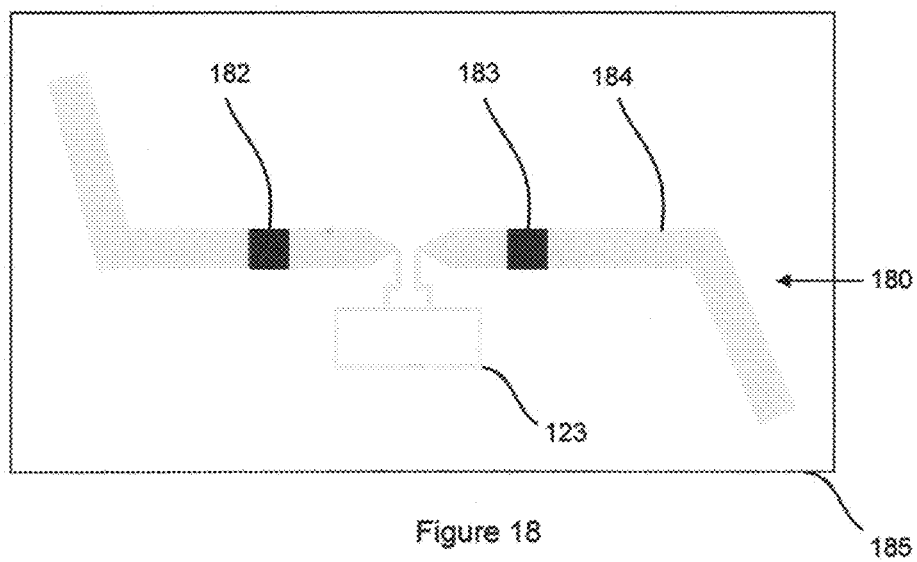
FIG. 18 illustrates a SAW sensor having dual sacrificial links in a single slope slanted dipole antenna.

FIG. 18 1 depicts an embodiment of a SAW corrosion sensor 180 with two (exposed) sacrificial links 182 and 183 and a dual slope slanted dipole antenna 184 after application of a conformal coating 185.

Figure 19:
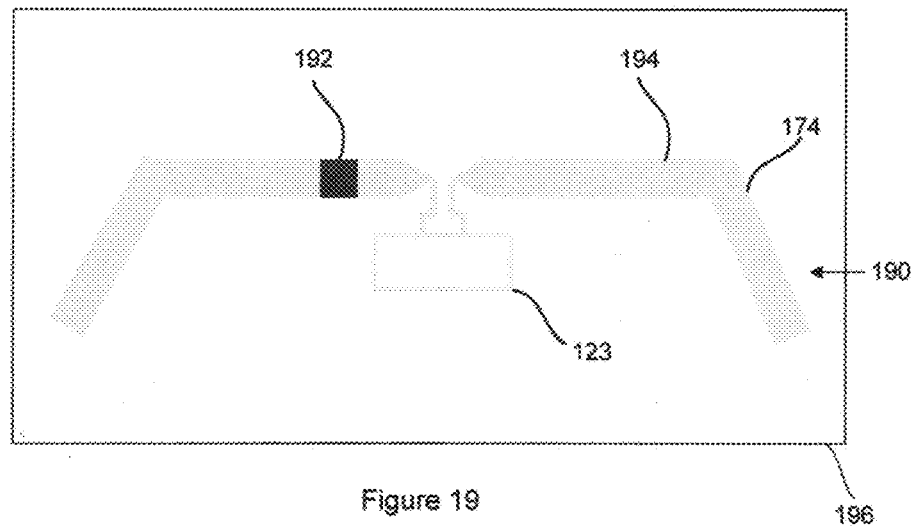
FIG. 19 illustrates a SAW sensor having a single sacrificial link in a dual slope slanted dipole antenna.

FIG. 19 depicts an embodiment of a SAW corrosion sensor 190 having a single sacrificial link 192 with a dual slope slanted dipole antenna 194 after application of a conformal coating 196.

Figure 20:
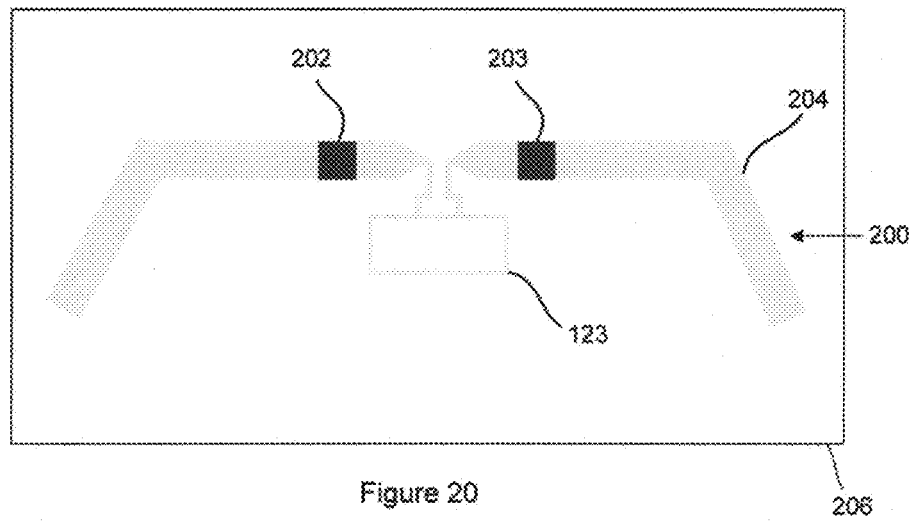
FIG. 20 illustrates a SAW sensor having dual sacrificial links in a dual slope slanted dipole antenna.

FIG. 20 depicts an embodiment of a SAW corrosion sensor 200 having dual sacrificial links 202 and 203 with a dual slope slanted dipole antenna 204 after application of a conformal coating 206.

Figure 21:
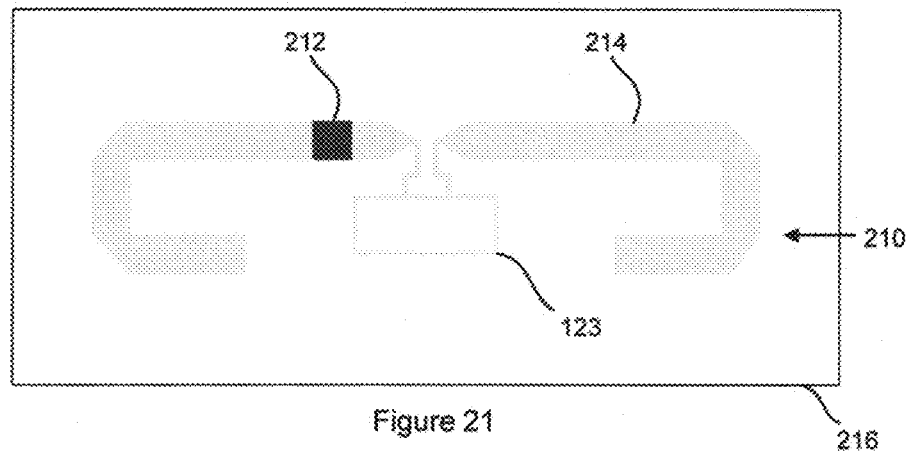
FIG. 21 illustrates a SAW sensor having a single sacrificial link in a folded dipole antenna.

FIG. 21 depicts an embodiment of a SAW corrosion sensor 210 having a single sacrificial link 212 in a folded dipole antenna 214 after application of a conformal coating 216.

Figure 22:
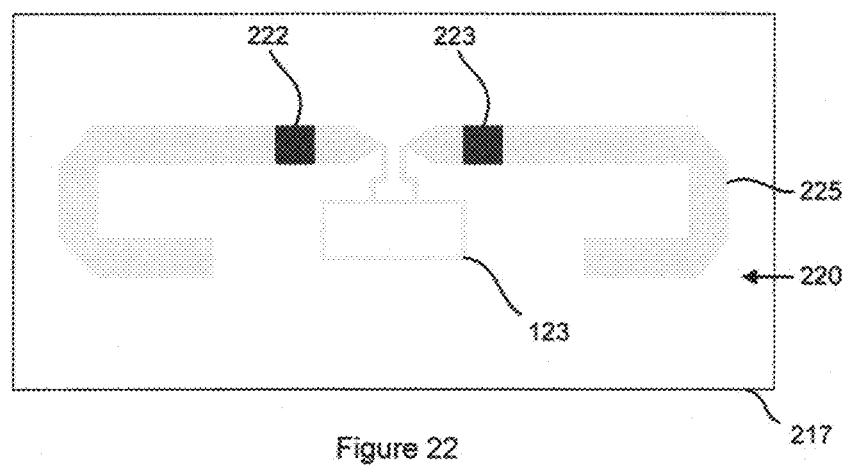
FIG. 22 illustrates a SAW sensor having dual sacrificial links in a folded dipole antenna.

FIG. 22 depicts an embodiment of a SAW corrosion sensor 220 having dual sacrificial links 222 and 223 in a folded dipole antenna 225 after application of a conformal coating 227.

Figure 23:
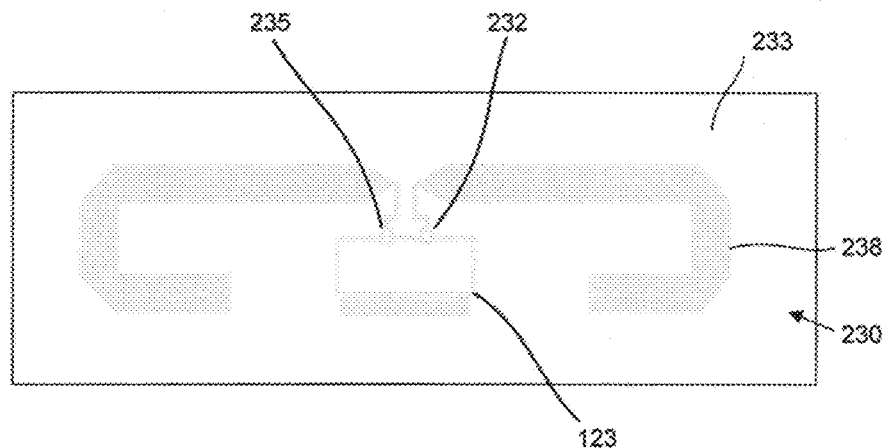
FIGS. 23 and 24 illustrate another embodiment of the present invention comprising a sacrificial link shorting the antenna terminals to prevent transmission of a return or echo signal.

FIG. 23 depicts a complement SAW corrosion sensor 230 prior to application of a protective coating. A sacrificial link 232 is formed or installed on a PCB 233 such that initially antenna ports 235 and 236 are shorted and the RF echo (i.e., return signal) is suppressed; no return echo signal is transmitted to the interrogation unit. When the sacrificial link 232 has been corroded and opened, an antenna 238 operates normally and the full antenna gain is available; the SAW sensor 230 responds with a suitable "full strength" return signal.

Thus any material of interest (e.g., a concrete structure) having a first corrosion sensor having an antenna that opens when corroded (i.e., no signal transmitted from the antenna when corroded) proximate a second corrosion sensor having an antenna that transmits only after corroded, results in one of the first and second sensors producing a return echo at all times. Each sensor has a unique identification and thus presenting redundant corrosion monitoring.

Figure 24:
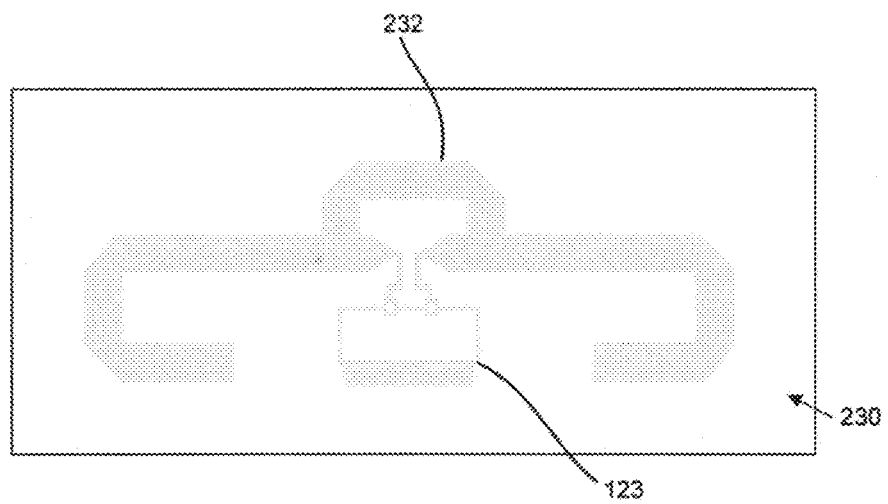

FIG. 24 depicts the sensor of FIG. 23 after application of a conformal coating 240 with the sacrificial link 232 closed.

Figure 25:
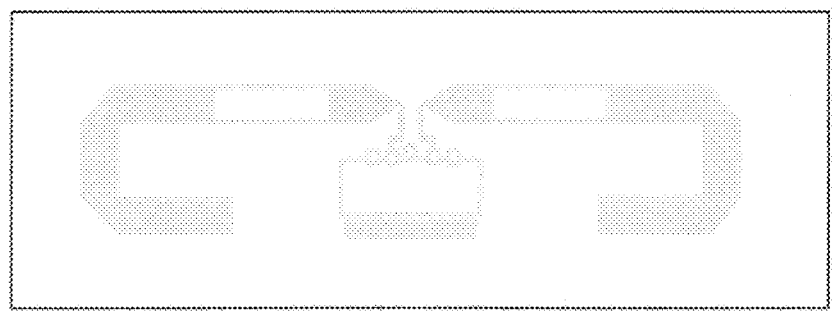
FIGS. 25 and 26 are photographs of a wireless corrosion sensor In accordance with common practice, the various described features are not drawn to scale, but are drawn to emphasize specific features relevant to the invention. Like reference characters denote like elements throughout the figures and text.

FIG. 25 is an illustration of a fully functional corrosion sensor according to the teachings of the present invention before application of a conformal coating.

Figure 26:
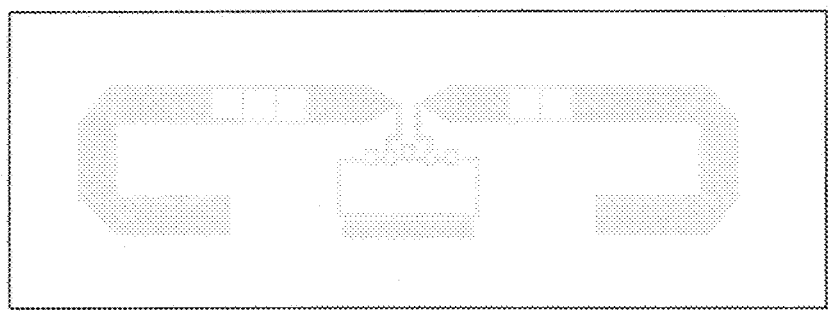

FIG. 26 depicts the sensor of FIG. 25 after application of the conformal coating. Contours of the unprotected sacrificial links can be seen.

Although described as a conformal coating, other protective material layers are known by those skilled in the art and can be used to protect the elements of the SAW corrosion detection device (except for the sacrificial links) of the present invention.

Although described in the context of a concrete corrosion sensor, the teachings of the present invention can be applied to any material for which it is desired to detect corrosion or monitor another material property. With respect to corrosion detection, the material properties of the antenna corrosive link(s) mimic properties of the material that is being monitored for corrosion.

Although described in the context of a dipole antenna, the teachings of the present invention can be applied to any antenna that can accept sacrificial links and that will operate at a degraded performance or not operate when the sacrificial links are open.

Although described as comprising one or two sacrificial links, more than two such links (connected in series or parallel, for example) may be used in a sensor of the present invention as suggested by the application.

While the invention has been described with reference to preferred embodiments, it will be understood by those skilled in the art that various changes may be made and equivalent elements may be substituted for elements thereof without departing from the scope of the present invention. The scope of the present invention further includes any combination of the elements from the various embodiments set forth herein. In addition, modifications may be made to adapt a particular situation to the teachings of the present invention without departing from its essential scope thereof. Therefore, it is intended that the invention not be limited to the particular embodiment disclosed as the best mode contemplated for carrying out this invention, but that the invention will include all embodiments falling within the scope of the claims.

What is claimed is:

1. A surface acoustic wave sensor disposed in or on a material, the sensor comprising;

an antenna comprising at least one antenna element and a sacrificial link comprising a portion of the at least one antenna element, wherein the sacrificial link is exposed to degrading elements within or on a surface of the material, and wherein operating characteristics of the antenna are responsive to a condition of the sacrificial link;

a surface acoustic wave transducer responsive to an interrogation signal received by the antenna, the transducer for generating an incident surface acoustic wave responsive to the interrogation signal;

a reflector responsive to the incident surface acoustic wave for creating a reflected surface acoustic wave;

the reflected surface acoustic wave received by the transducer;

the transducer for creating a response signal responsive to the reflected surface acoustic wave; and the response signal transmitted from the antenna, characteristics of the response signal dependent on a condition of the sacrificial link.

2. The surface acoustic wave sensor of claim 1 wherein a characteristic of the response signal is dependent on a degree of corrosion of the material.

3. The surface acoustic wave sensor of claim 1 wherein the degrading elements comprise corrosion-causing elements.

4. The surface acoustic wave sensor of claim 1 wherein the material comprises concrete with rebars embedded therein and the sacrificial link exhibits corrosive properties similar to corrosive properties of the rebars.

5. The surface acoustic wave sensor of claim 1 wherein the characteristics of the response signal comprise a degraded response signal when the sacrificial link is degraded.

6. The surface acoustic wave sensor of claim 1 wherein the characteristics of the response signal comprise no response signal when the sacrificial link is open.

7. The surface acoustic wave sensor of claim 1 wherein the antenna comprises one of a linear dipole, a single slope slanted dipole, a dual slope slanted dipole and a folded dipole, and wherein the sacrificial link is disposed in one element of the linear dipole, one element of the single slope slanted dipole, one element of the dual slope slanted dipole or one element of the folded dipole.

8. The surface acoustic wave sensor of claim 1 embedded in concrete with the sacrificial links exhibiting corrosion properties similar to corrosion properties of rebars also embedded in the concrete.

9. The surface acoustic wave sensor of claim 1 wherein characteristics of the response signal indicate a condition of the material proximate the sacrificial link.

10. The surface acoustic wave sensor of claim 1 further comprising an insulating layer for preventing the degrading elements from reaching the surface acoustic wave sensor with the exception of the sacrificial link.

11. A surface acoustic wave sensor for monitoring a condition of rebars within concrete, the sensor comprising:

an antenna comprising at least one antenna element and a sacrificial link comprising a portion of the at least one antenna element, wherein the sacrificial link is exposed to degrading elements within or on a surface of the concrete, and wherein operating characteristics of the antenna are responsive to a condition of the sacrificial link;

a surface acoustic wave transducer responsive to an interrogation signal received by the antenna, the transducer for generating an incident surface acoustic wave responsive to the interrogation signal;

a reflector responsive to the incident surface acoustic wave for creating a reflected surface acoustic wave;

the reflected surface acoustic wave received by the transducer;

the transducer for creating a response signal responsive to the reflected surface acoustic wave;

the response signal transmitted from the antenna, characteristics of the response signal dependent on a condition of the sacrificial link and thereby dependent on a condition of the rebars; and an insulating layer over the surface acoustic wave sensor except for the sacrificial link.

\* \* \* \* \*